United States Patent [19]
Alferness

[11] Patent Number: 5,332,400
[45] Date of Patent: Jul. 26, 1994

[54] ATRIAL DEFIBRILLATOR AND METHOD FOR PROVIDING PRE-CARDIOVERSION WARNING

[75] Inventor: Clifton A. Alferness, Redmond, Wash.

[73] Assignee: InControl, Inc., Redmond, Wash.

[21] Appl. No.: 996,656

[22] Filed: Dec. 24, 1992

[51] Int. Cl.⁵ .............................................. A61B 5/04
[52] U.S. Cl. ...................................................... 607/5
[58] Field of Search ................................... 607/5, 6, 7

[56] References Cited
U.S. PATENT DOCUMENTS
4,295,474 10/1981 Fischell .................... 607/5

Primary Examiner—William E. Kamm
Assistant Examiner—Scott M. Getzow
Attorney, Agent, or Firm—Foley & Lardner

[57] ABSTRACT

An implantable atrial defibrillator provides cardioverting electrical energy to the atria of a patient's heart in need of cardioversion and a precardioversion warning to the patient. The atrial defibrillator includes a detector for detecting atrial activity of the patient's heart, and an atrial fibrillation detector responsive to the atrial activity detector for determining when the atria of the patient's heart are in need of cardioversion. A cardioverter responsive to the atrial fibrillation detector, applies warning electrical energy to the atria of the patient's heart when the atria are in need of cardioversion and thereafter applies cardioverting electrical energy to the atria. The warning electrical energy is of insufficient quantity to intentionally cardiovert the atria but of sufficient quantity so as to be discernable by the patient.

28 Claims, 3 Drawing Sheets

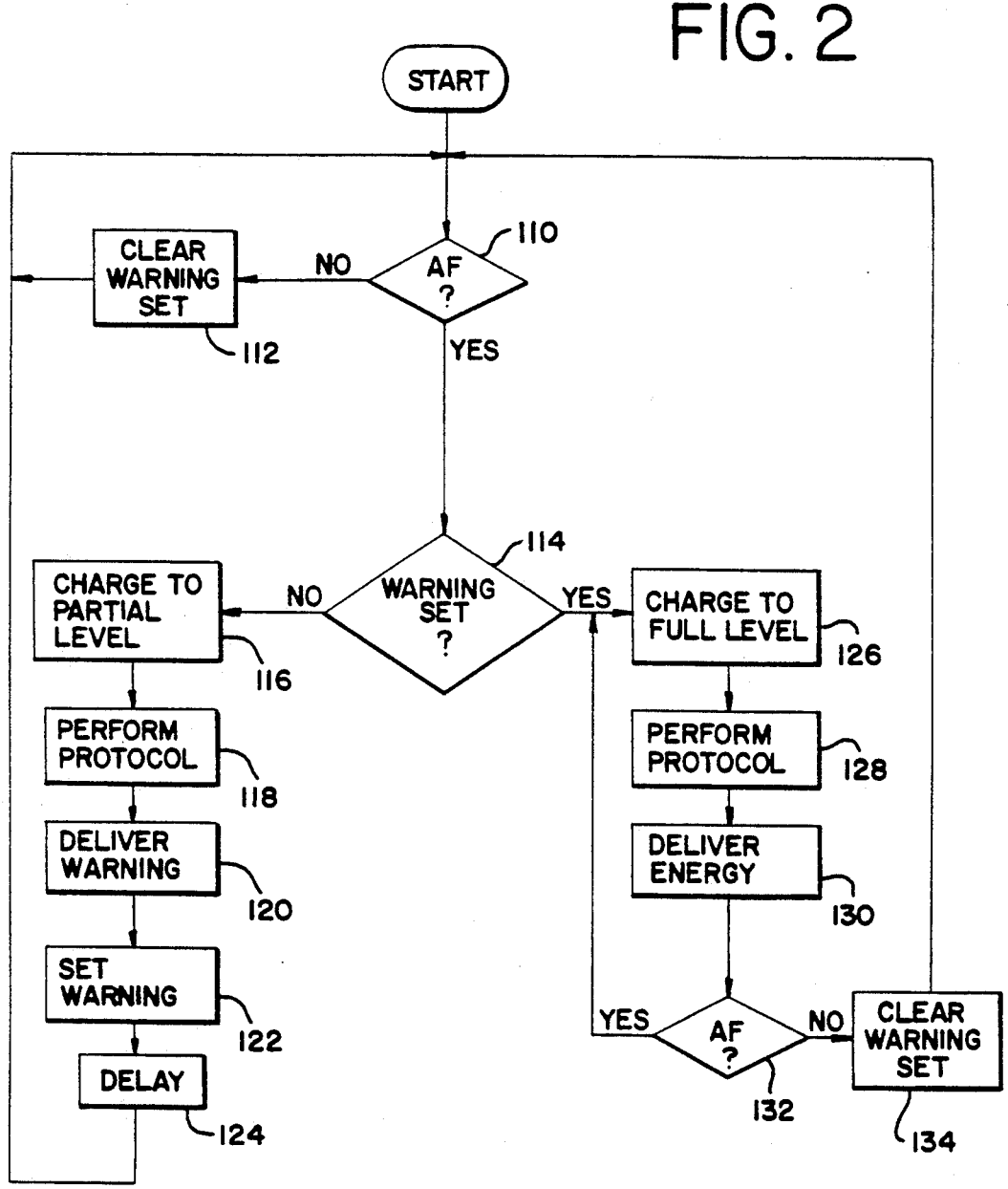

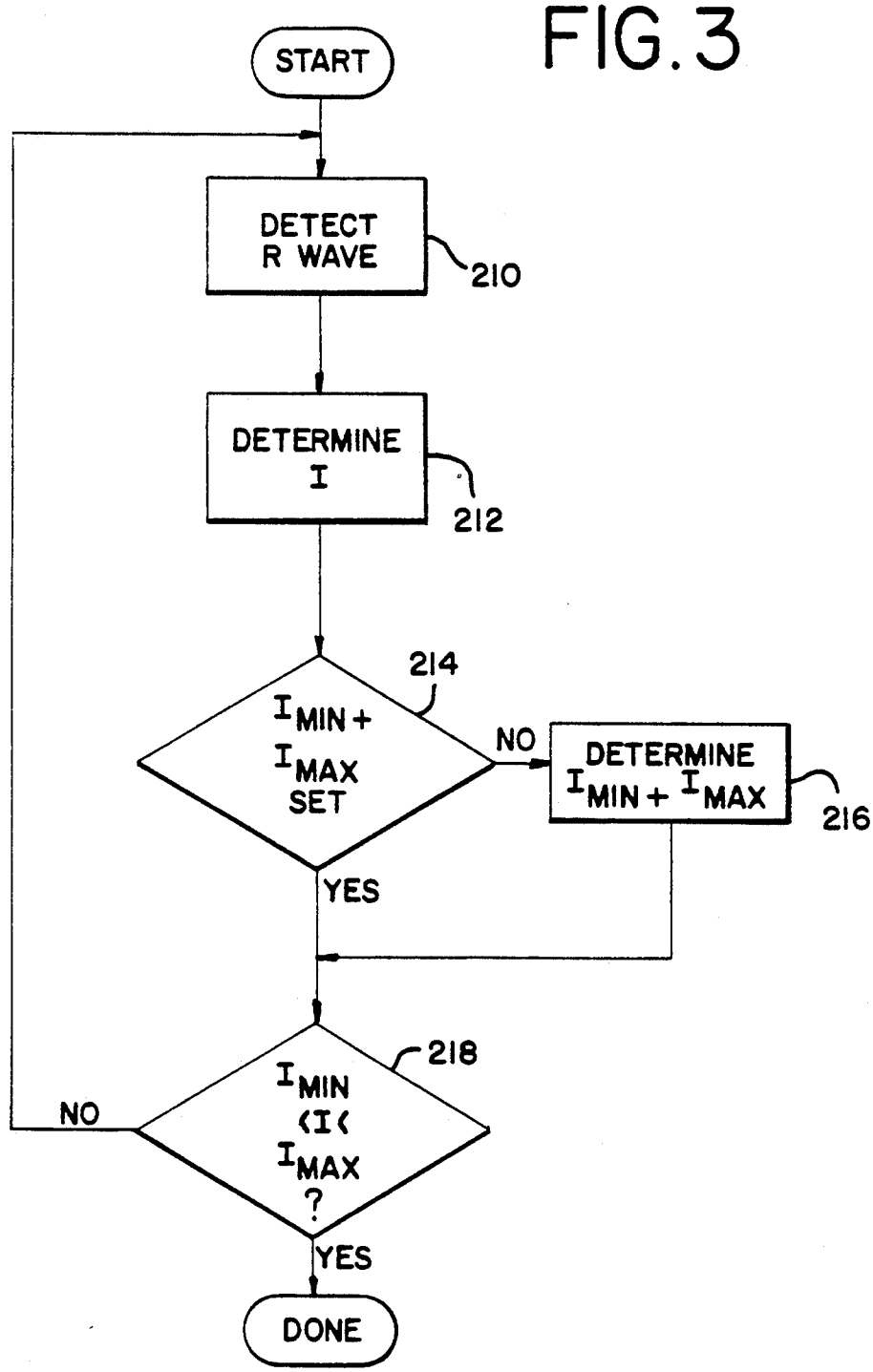

ATRIAL DEFIBRILLATOR AND METHOD FOR PROVIDING PRE-CARDIOVERSION WARNING

BACKGROUND OF THE INVENTION

The present invention generally relates to an implantable device for applying cardioverting electrical energy to at least one chamber of a patient's heart in need of cardioversion and a warning to the patient indicating the imminent delivery of the cardioverting energy. The present invention is more particularly directed to a fully automatic implantable atrial defibrillator which exhibits improved safety by providing warning electrical energy to the patient when the patient's heart is in need of cardioversion and at least a predetermined time before the delivery of cardioverting electrical energy to the atria of the patient's heart. The warning electrical energy is of a quantity which is less discomforting than the quantity required to cardiovert the atria. More specifically, the warning electrical energy is of sufficient quantity so as to be readily discernable by the patient but of insufficient quantity to intentionally cardiovert the atria of the heart.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator with an external magnet.

Improved implantable atrial defibrillators and lead systems which exhibit automatic operation are fully described in copending U.S. applications, Ser. No. 07/685,130, filed Apr. 12, 1991, in the names of John M. Adams and Clifton A. Alferness for IMPROVED ATRIAL DEFIBRILLATOR AND METHOD and Ser. No. 07/856,514, filed Mar. 24, 1992, in the names of John M. Adams, Clifton A. Alferness, and Paul E. Kreyenhagen for IMPROVED ATRIAL DEFIBRILLATOR, LEAD SYSTEMS, AND METHOD, which applications are assigned to the assignee of the present invention and incorporated herein by reference. The atrial defibrillator disclosed in the aforementioned referenced applications, are truly automatic by including an atrial fibrillation detector which, responsive to sensed atrial activity, determines when the atria of the heart are in need of cardioversion. When the atrial fibrillation detector determines that the atria are in fibrillation and thus in need of cardioversion, the atrial fibrillation detector causes a cardioverter stage to deliver defibrillating or cardioverting electrical energy to the atria in timed relation to a detected ventricular electrical activation (R wave) of the heart. As a result, the atria are automatically and safely cardioverted.

Unfortunately, the quantity of electrical energy which is required to cardiovert or defibrillate the atria is sufficient, in most cases, to cause a sudden pain in the patient's chest area or stun the patient. In addition, the successful cardioversion or defibrillation of the atria may also result in a rapid decrease in the patient's heart rate from a high and possibly variable heart rate. This rapid change in heart rate can, for some patients, cause discomfort or even temporary dizziness. As a result, it would be highly desirable to provide a warning to a patient prior to the delivery of cardioverting or defibrillating electrical energy to the patient's atria.

The atrial defibrillator and method of the present invention provide such a warning. The warning is in the form of electrical energy applied to internal tissue of the patient and being of a quantity so as to be discernable by the patient without pain or other undesirable effects. The warning also provides a sufficient time in advance of the delivery of the cardioverting electrical energy to afford the patient with an opportunity to prepare for it. For example, if the patient is standing or walking and receives the warning, the patient may wish to find a place to sit in preparation. As another example, if the patient is driving an automobile and receives the warning, the patient may wish to safely pull off the road and park in preparation. As a result, in providing the warning to the patient, the atria of the patient may be cardioverted with a degree of increased safety not heretofore possible.

SUMMARY OF THE INVENTION

The present invention therefore provides an implantable cardiac device for providing cardioverting electrical energy to at least one chamber of a patient's heart in need of cardioversion. The device includes detecting means for detecting activity of the at least one chamber of the patient's heart, determining means responsive to the detecting means for determining when the at least one chamber of the patient's heart is in need of cardioversion, and cardioverting means responsive to the determining means for applying the cardioverting electrical energy to the at least one chamber of the patient's heart when the at least one chamber is in need of cardioversion. The device further includes warning means for applying warning electrical energy to internal tissue of the patient prior to the cardioverting means applying the cardioverting electrical energy to the at least one chamber of the heart. The warning electrical energy is of insufficient quantity to cardiovert the at least one chamber but is of sufficient quantity so as to be discernable by the patient.

The invention further provides an implantable atrial defibrillator for providing cardioverting electrical energy to the atria of a patient's heart in need of cardioversion. The atrial defibrillator includes detecting means for detecting atrial activity of the patient's heart, atrial fibrillation detecting means responsive to the detecting means for determining when the atria of the patient's heart are in need of cardioversion, and cardioverting means responsive to the atrial fibrillation detecting means for applying warning electrical energy to the atria of the patient's heart when the atria are in need of cardioversion and for thereafter applying cardioverting electrical energy to the atria. The warning electrical energy is of insufficient quantity to cardiovert the atria but is of sufficient quantity so as to be discernable by the patient.

The present invention further provides a method of providing cardioverting electrical energy to at least one chamber of a patient's heart in need of cardioversion. The method includes the steps of detecting activity of the at least one chamber of the patient's heart, determining from the detected activity when the at least one chamber of the patient's heart is in need of cardioversion, applying warning electrical energy to internal tissue of the patient when the at least one chamber of the patient's heart is in need of cardioversion, and thereafter applying the cardioverting electrical energy to the at least one chamber of the patient's heart. The warning electrical energy is of insufficient quantity to cardiovert the at least one chamber but is of sufficient quantity so as to be discernable by the patient.

The present invention still further provides a method for providing cardioverting electrical energy to the atria of a patient's heart in need of cardioversion. The method includes the steps of detecting atrial activity of the patient's heart, determining from the detected atrial activity when the atria of the patient's heart are in need of cardioversion, applying warning electrical energy to the atria of the patient's heart when the atria are in need of cardioversion, and thereafter applying cardioverting electrical energy to the atria of the patient's heart to cardiovert the atria. The warning electrical energy is of insufficient quantity to cardiovert the atria but is of sufficient quantity so as to be discernable by the patient.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

FIG. 2 is a flow diagram illustrating the manner in which the atrial defibrillator of FIG. 1 may be implemented in accordance with the present invention for providing a warning to the patient before applying defibrillating or cardioverting electrical energy to the atria of the heart; and FIG. 3 is a flow diagram illustrating the manner in which the atrial defibrillator may be implemented in executing a protocol before providing the warning and the cardioverting electrical energy to assure that the patient's heart is not in a vulnerable condition.

DETAILED DESCRIPTION OF THE PREFERRED EMBODIMENT

Figure 1:
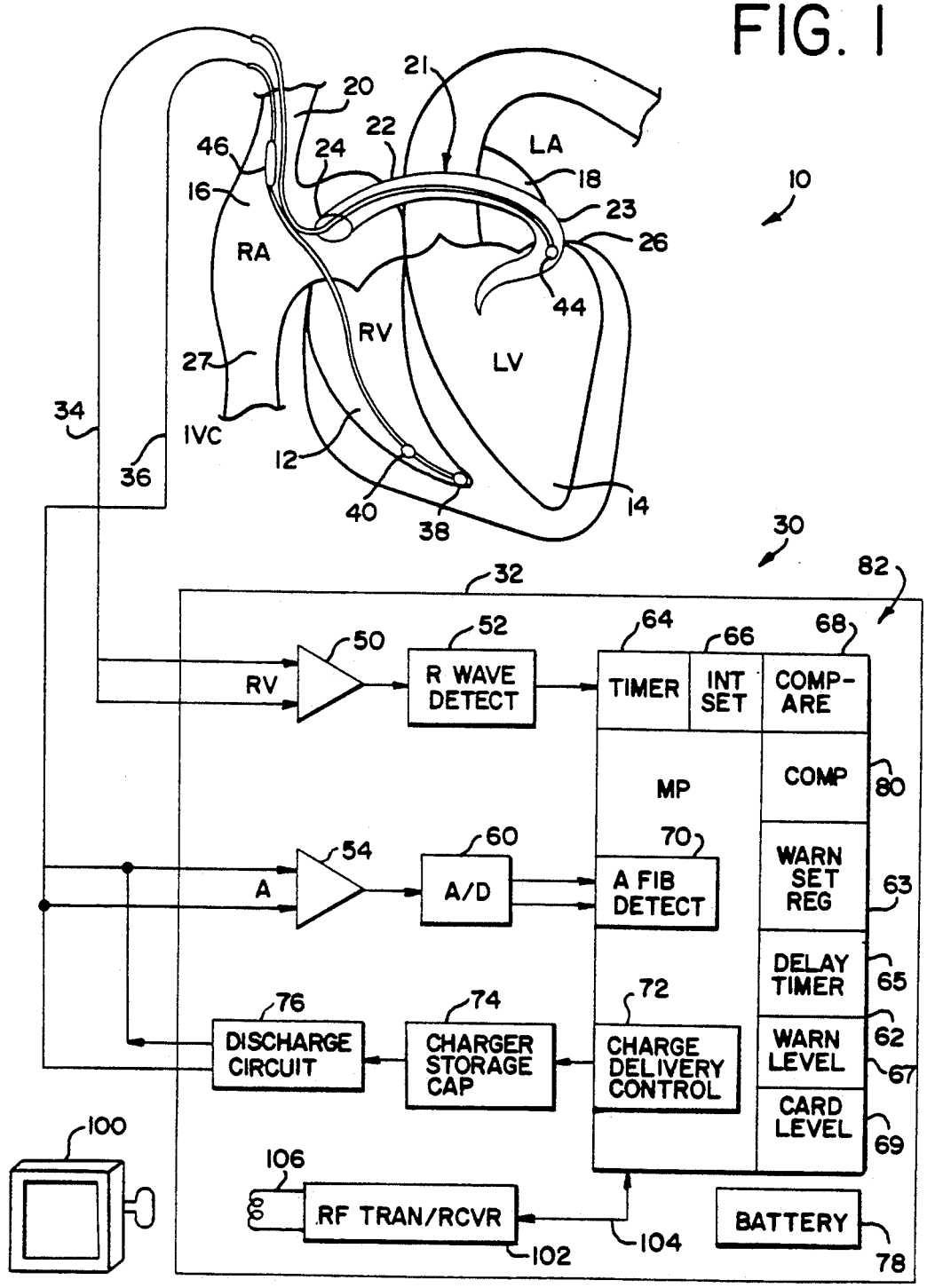
FIG. 1 is a schematic block diagram of a fully implantable atrial defibrillator embodying the present invention for applying defibrillating electrical energy to the atria of a patient's heart and which is shown in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27. In addition, as used herein, the term "ventricular activations" denotes R waves of the heart cardiac cycle which induce depolarizations of the ventricles 12 and 14.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial bi-polar lead having electrodes 38 and 40 arranged for establishing electrical contact with the right ventricle 12 of the heart 10. The electrodes 38 and 40 permit bi-polar sensing of ventricular activations in the right ventricle. As illustrated, the lead 34 is preferably fed through the superior vena cava 20, into the right atrium 16, and then into the right ventricle 12 as illustrated.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery of defibrillating electrical energy to the atria and, in accordance with this preferred embodiment, warning electrical energy to the atria. Because the first electrode 44 is located beneath the left atrium 18 near the left ventricle 14 and the second electrode 46 is within the right atrium 16, the cardioverting electrical energy, when applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy of the atria of the heart.

Within the enclosure 32, the atrial defibrillator 30 includes a first sense amplifier 50, an R wave detector 52, and a second sense amplifier 54. The first sense amplifier 50 and the R wave detector 52 form a first detecting means which together with the first lead 34 to which sense amplifier 50 is coupled, senses ventricular activations of the right ventricle 12. The second sense amplifier 54 forms a second detecting means which, together with the first electrode 44 and second electrode 46 of the second lead 36 to which it is coupled detects atrial activity of the heart.

The output of the first sense amplifier 50 is coupled to the R wave detector 52. The R wave detector 52 is of the type well known in the art which provides an output pulse upon the occurrence of an R wave being sensed during a cardiac cycle of the heart. The output of the second sense amplifier 54 is coupled to an analog to digital converter 60 which converts the analog signal representative of the atrial activity of the heart being detected to digital samples for further processing in a manner to be described hereinafter.

The enclosure 32 of the atrial defibrillator 30 further includes a microprocessor 62. The microprocessor 62 is preferably implemented in a manner as disclosed in the aforementioned copending U.S. applications, Ser. Nos. 07/685,130 and 07/856,514 and further as described hereinafter with respect to the flow diagrams of FIGS. 2 and 3. The implementation of the microprocessor 62 in accordance with this embodiment of the present invention results in a plurality of functional stages. The stages include a warning set register 63, a timer 64, a delay timer 65, an interval set stage 66, a warning level set stage 67, a comparator stage 68, a cardioversion level set stage 69, an atrial arrhythmia detector in the form of an atrial fibrillation detector 70, a charge delivery and energy control stage 72 and a computation stage 80.

The microprocessor 62 is arranged to operate in conjunction with a memory (not shown) which may be coupled to the microprocessor 62 by a multiple-bit address bus (not shown) and a bi-directional multiple-bit databus (not shown). This permits the microprocessor 62 to address desired memory locations within the memory for executing write or read operations. During a write operation, the microprocessor stores data, such as time intervals or operating parameters in the memory at the addresses defined by multiple-bit addresses conveyed over the address bus and coveys the data to the memory over the multiple-bit data bus. During a read operation, the microprocessor 62 obtains data from the memory at the storage locations identified by the multiple-bit addresses provided over the address bus and receives the data from the memory over the bi-directional data bus.

As will be seen hereinafter, the warning set register 63, the delay timer 65, and the warning level set stage 67 are utilized for applying warning electrical energy to the atria of the patient when the atrial fibrillation detector 70 determines that the atria are in fibrillation. The warning level stage 67 sets the quantity of electrical energy to be applied to the atria for warning the patient that atrial fibrillation has been detected and that cardioverting electrical energy will be applied to the patient's atria. The warning electrical energy is preferably of insufficient quantity to intentionally cardiovert the atria but of sufficient quantity to be discernable by the patient. For example, the warning electrical energy may be of a quantity on the order of 0.1 joule.

After the warning is delivered to the patient, the warning register 63 is set to indicate that the patient has received the warning. Immediately thereafter, the delay timer 65 starts timing a delay period. The delay period defines a time interval from when the patient receives the warning to when the patient should first expect to receive the cardioverting electrical energy. The delay time is preferably programmable between one minute and twenty minutes to afford sufficient time to permit the patient to prepare for receiving the cardioverting electrical energy.

Before the warning electrical energy is applied and after the warning electrical energy is applied but before the cardioverting electrical energy is applied, the timer 64, interval set stage 66, the comparator stage 68 and computation stage 80, which form a protocol means 82, implement a protocol to be described with reference to FIG. 3 which assures that the patient's heart is not in a vulnerable condition when the warning and cardioverting electrical energy are applied to the patient's atria. As a result, the warning and cardioverting electrical energy will be safely applied. As a further result, the cardioverting electrical energy may be applied at a time following the warning which is longer than the programmed delay time if the protocol criteria are not satisfied immediately after the delay time has elapsed. Hence, the delay time sets a minimum time after the warning in which the patient should expect to receive the cardioverting electrical energy.

Following the warning and after the delay time has elapsed and the protocol criteria have been satisfied, the cardioverting electrical energy is applied to the patient's atria. The quantity of cardioverting electrical energy is set by the cardioversion level set stage 69 and may be between 0.5 and 3 joules and more preferably, between 0.5 and one joule with the placement of electrodes 44 and 46 as previously described in accordance with this preferred embodiment.

For entering operating parameters into the microprocessor 62, such as a delay time for delay timer 65, the warning level for warning level set stage 67 or the cardioversion level for cardioversion level set stage 69, the microprocessor 62 receives programmable operating parameters from an external controller 100 which is external to the skin of the patient. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100 or for receiving programming parameters from the external controller 100 which the receiver/transmitter 102 then conveys to the microprocessor 62 for storage in interval memory, such as stages 67 and 69, or in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosure 32 and for transmitting data to the external controller 100 from the implanted enclosure 32. One such communication system is disclosed, for example, in U.S. Pat. No. 4,586,508.

To complete the identification of the various structural elements within the enclosure 32, the atrial defibrillator 30 further includes a charger and storage capacitor circuit 74 of the type well known in the art. The circuit 74 charges a storage capacitor to a predetermined voltage level, either a full voltage level for cardioverting the atria or a partial voltage level for providing the warning to the patient. The enclosure 32 further includes a discharge circuit 76. The discharge circuit 76 discharges the storage capacitor within circuit 74 by a predetermined amount to provide a controlled quantity of discharged warning or cardioverting electrical energy when required to the atria of the heart. To that end, the discharge circuit 76 is coupled to the first electrode 44 and the second electrode 46 of the second lead 36 for applying the warning and cardioverting or defibrillating electrical energy to the atria. Lastly, the defibrillator 30 includes a depletable power source 78, such a lithium battery, for providing power to the electrical components of the atrial defibrillator 30.

The sense amplifier 50 and the R wave detector 52 continuously detect the occurrence of ventricular activations of the right ventricle 12. As disclosed in the aforementioned copending U.S. applications Ser. Nos. 07/685,130 and 07/856,514, incorporated herein by reference, when the time intervals between immediately successive R waves indicate the probability of an episode of atrial fibrillation, the microprocessor 62 enables the atrial fibrillation detector 70, sense amplifier 54, and the analog to digital converter 60. The operation of the atrial defibrillator 30 then enters the implementation illustrated in the flow diagram of FIG. 2.

Referring now to FIG. 2, the microprocessor 62 first, and more particularly the atrial fibrillation detector 70, in step i 10, determines whether the atria are in fibrillation and thus in need of cardioversion. If the atrial fibrillation detector 70 determines that the atria are not in fibrillation, the warning set register 63 is cleared in step 112 and the microprocessor returns. However, if atrial fibrillation is detected in step 110, the microprocessor proceeds to step 114 to determine if the warning set register 63 is set. If the warning set register is not set, indicating that a warning has not been provided to the patient, the microprocessor proceeds to step 116 to prepare for delivering the warning to the patient.

In performing step 116, the microprocessor causes the capacitor within circuit 74 to be charged to a partial level. The partial level is slightly above that required to deliver the warning electrical energy to the patient's atria. When the capacitor is charged to the partial level, the microprocessor enters the safety protocol in step 118 which will now be described with reference to FIG. 3.

Referring now to FIG. 3, the safety protocol is initiated in step 210 with a ventricular activation (R wave) being detected by sense amplifier 50 and the R wave detector 52. The microprocessor then in step 212 determines the time between the last two immediately successive detected R waves. In doing so, the microprocessor interrogates the timer 64 which times, responsive to the sense amplifier 50 and R wave detector 52, the time between immediately successive ventricular activations of the heart 10. Once the last R wave to R wave time interval (I) is determined in step 212, the microprocessor proceeds to step 214 to determine whether minimum and maximum time intervals have been set. In performing step 214, the microprocessor interrogates the interval set stage 66 to determine if the minimum and maximum time intervals have been set. The minimum and maximum time intervals may be set from external to the implanted atrial defibrillator 30 by means of the external controller 100 and the transmitter/receiver 102. If the minimum and maximum time intervals have not been set from external to the atrial defibrillator 30, the atrial defibrillator then determines the minimum and maximum time intervals in step 216. In performing step 216, the computation stage 80 computes the average cardiac cycle interval responsive to and based upon a last predetermined number, such as eight, consecutive R waves detected by sense amplifier 50 and R wave detector 52 and timed by timer 64. Once the average cardiac interval is determined, the microprocessor sets the minimum time interval equal to the average cardiac interval and the computation stage 80 computes the maximum time interval based upon a multiple of the computed average cardiac cycle interval. In accordance with this preferred embodiment, the maximum time interval is preferably the computed average cardiac cycle interval multiplied by 2.0. In accordance with this preferred embodiment, the minimum time interval may be in the range of 300 to 500 milliseconds and the maximum time interval may be in the range of 600 milliseconds to 1 second.

Once the minimum and maximum time intervals are determined in step 216 or if the minimum and maximum time intervals are otherwise preselected as previously described, the atrial defibrillator then proceeds to step 218 to determine if the time between the last two immediately successive ventricular activations as determined in step 212 is greater than the minimum time interval and less than the maximum time interval. If it is not, the microprocessor returns to repeat the foregoing steps because the present cardiac rate is too high or because the present cardiac rate is suspected to be highly variable. In either case, a vulnerable R on T condition may be present indicating that electrical energy should not be applied to the heart at this time. If in step 218 the microprocessor 62 determines that the time between the last two immediately successive ventricular activations is greater than the preselected minimum time interval ($I_{min}$) and less than the preselected maximum time interval ($I_{max}$), the safety protocol is completed and the microprocessor proceeds to step 120 of FIG. 2.

In step 120, the charge delivery control stage 72 of microprocessor 62 causes the discharge circuit 76 to immediately discharge the electrical energy stored in the storage capacitor of circuit 74 in a controlled manner for applying the warning electrical energy to the atria 16 and 18 of the heart 10. Since the microprocessor 62 is able to complete steps 212 through 218 of the safety protocol very quickly after the occurrence of the last detected ventricular activation in step 210, the discharge circuit 76 will apply the warning electrical energy and, as will be seen hereinafter, the cardioverting electrical energy to the atria of the heart, substantially coincident or in synchronism with the last detected ventricular activation. As a result, the safety protocol of FIG. 2 precludes the application of electrical energy to the atria of the heart in the presence of a possible vulnerable condition resulting from a cardiac rate which is too high or a cardiac rate which is suspected of being highly variable.

After the warning electrical energy is delivered in step 120, the microprocessor then in step 122 sets the warning set register 63 to indicate that the warning has been delivered. It then proceeds to step 124 wherein the delay timer 65 is started and times the previously set delay time of, for example, between one minute and twenty minutes.

After the predetermined delay time has elapsed, the microprocessor returns to step 110 for the atrial fibrillation detector 70 to once again detect for atrial fibrillation. If the atrial fibrillation has ceased, the warning set register 63 is cleared in step 112. If the atria are still in fibrillation, step 114 is performed again to determine if the warning set register 63 is set. Since, in this scenario the warning set register 63 is set indicating that a warning has been delivered, the microprocessor proceeds to step 126. In step 126, the capacitor of circuit 74 is charged to the full level for delivering the cardioverting electrical energy to the atria. The full level is preferably slightly greater than the preselected quantity of cardioverting electrical energy. When step 126 is completed, the safety protocol of FIG. 3 is once again performed in step 128.

When the safety protocol is completed in step 128, the cardioverting electrical energy is then delivered to the atria in step 130. In performing step 130, the discharge circuit 76 controllably discharges the capacitor of circuit 74 until the preselected quantity of cardioversion electrical energy has been delivered to the atria by electrodes 44 and 46.

After the cardioverting electrical energy is applied to the atria, the atrial fibrillation detector 70 is once again interrogated in step 132 to determine if the application of cardioverting electrical energy to the atria was successful in cardioverting the atria. If it was not, the atrial defibrillator returns to step 126 to once again charge the capacitor to the full level and repeat steps 128, 130, 132.

If the application of the cardioverting electrical energy was successful in arresting the atrial fibrillation, the warning set register 63 is cleared in step 134. The microprocessor then returns to step 110. When the cardioversion is successful, the atrial fibrillation detector 70 is deactivated and the atrial defibrillator returns to normal monitoring. Hence, the warning electrical energy is applied only once for each detected atrial fibrillation in accordance with this preferred embodiment.

As can be seen from the foregoing, the present invention provides an improved atrial defibrillator which provides a pre-cardioversion warning to the patient and permits sufficient time for the patient to prepare for receiving the cardioverting electrical energy. Further safety is provided by the safety protocol which assures that electrical energy is only applied when the patient's heart is not in a vulnerable condition.

While a particular embodiment of the present invention has been shown and described, modifications may be made. For example, the patient warning of the present invention may be utilized to advantage in implantable cardiac devices other than atrial defibrillators. For example, the present invention may be employed to advantage in implantable devices which cardiovert ventricular tachycardia. Hence, it is therefore intended in the appended claims to cover all such changes and modifications which fall within the true spirit and scope of the invention.

What is claimed is:

1. An implantable cardiac device for providing cardioverting electrical energy to at least one chamber of a patient's heart in need of cardioversion, said device comprising:
   detecting means for detecting activity of the at least one chamber of the patient's heart;
   determining means responsive to said detecting means for determining when the at least one chamber of the patient's heart is in need of cardioversion;
   cardioverting means responsive to said determining means for applying said cardioverting electrical energy to the at least one chamber of the patient's heart when the at least one chamber is in need of cardioversion; and
   warning means for applying warning electrical energy to the at least one chamber of the patient's heart prior to said cardioverting means applying said cardioverting electrical energy to said at least one chamber, said warning electrical energy being of insufficient quantity to cardiovert the at least one chamber but of sufficient quantity so as to be discernable by the patient.

2. A cardiac device as defined in claim 1 wherein said warning means is also responsive to said determining means for applying said warning electrical energy when the at least one chamber of the patient's heart is in need of cardioversion.

3. A device as defined in claim 1 further including delay means for delaying the application of said cardioverting energy by said cardioverting means until after at least a predetermined delay time elapses after the application of said warning electrical energy.

4. A device as defined in claim 3 wherein said predetermined delay time is between one minute and twenty minutes.

5. An implantable system for providing cardioverting electrical energy to at least one chamber of a patient's heart in need of cardioversion, said system comprising:
   a cardiac device, said device including,
   detecting means for detecting activity of the at least one chamber of the patient's heart;
   determining means responsive to said detecting means for determining when the at least one chamber of the patient's heart is in need of cardioversion;
   cardioverting means responsive to said determining means for applying said cardioverting electrical energy to the at least one chamber of the patient's heart when the at least one chamber is in need of cardioversion; and
   warning means for applying warning electrical energy to internal tissue of the patient prior to said cardioverting means applying said cardioverting electrical energy to said at least one chamber, said warning electrical energy being of insufficient quantity to cardiovert the at least one chamber but of sufficient quantity so as to be discernable by the patient; and
   lead means for establishing electrical contact with said at least one chamber and wherein said warning electrical energy and said cardioverting electrical energy are both applied to said lead means.

6. An implantable cardiac device for providing cardioverting electrical energy to at least one chamber of a patient's heart in need of cardioversion, said device comprising:
   detecting means for detecting activity of the at least one chamber of the patient's heart;
   determining means responsive to said detecting means for determining when the at least one chamber of the patient's heart is in need of cardioversion;

cardioverting means responsive to said determining means for applying said cardioverting electrical energy to the at least one chamber of the patient's heart when the at least one chamber is in need of cardioversion;

warning means for applying warning electrical energy to internal tissue of the patient prior to said cardioverting means applying said cardioverting electrical energy to said at least one chamber, said warning electrical energy being of insufficient quantity to cardiovert the at least one chamber but of sufficient quantity so as to be discernable by the patient; and protocol means for determining that the patient's heart is in a nonvulnerable condition and wherein said protocol means is activated prior to the application of each said warning electrical energy and said cardioverting electrical energy.

7. An implantable atrial defibrillator for providing cardioverting electrical energy to the atria of a patient's heart in need of cardioversion, said atrial defibrillator comprising:

detecting means for detecting atrial activity of the patient's heart;

atrial fibrillation detecting means responsive to said detecting means for determining when the atria of the patient's heart are in need of cardioversion; and cardioverting means responsive to said atrial fibrillation detecting means for applying warning electrical energy to the atria of the patient's heart when the atria are in need of cardioversion and for thereafter applying cardioverting electrical energy to the atria, said warning electrical energy being of insufficient quantity to cardiovert the atria but of sufficient quantity so as to be discernable by the patient.

8. An atrial defibrillator as defined in claim 7 wherein said cardioverting means is also responsive to said atrial fibrillation detecting means determining that the atria are in need of cardioversion after the application of said warning electrical energy and before applying said cardioverting electrical energy to the atria of the patient's heart.

9. An atrial defibrillator as defined in claim 7 further including delay means for delaying the application of said cardioverting energy by said cardioverting means until after at least a predetermined delay time elapses after the application of said warning electrical energy.

10. An atrial defibrillator as defined in claim 9 wherein said predetermined delay time is between one minute and twenty minutes.

11. An atrial defibrillator as defined in claim 7 further including protocol means for determining that the patient's heart is in a nonvulnerable condition and wherein said protocol means is activated prior to the application of each said warning electrical energy and said cardioverting electrical energy.

12. An atrial defibrillator as defined in claim 7 wherein said warning electrical energy has a quantity on the order of 0.1 joule and wherein said cardioverting electrical energy has a quantity between 0.5 and one joule.

13. An implantable system for providing cardioverting electrical energy to the atria of a patient's heart in need of cardioversion, said system comprising:

an atrial defibrillator, said defibrillator including, detecting means for detecting atrial activity of the patient's heart, atrial fibrillation detecting means responsive to said detecting means for determining when the atria of the patient's heart are in need of cardioversion, and cardioverting means responsive to said atrial fibrillation detecting means for applying warning electrical energy to the atria of the patient's heart when the atria are in need of cardioversion and for thereafter applying cardioverting electrical energy to the atria, said warning electrical energy being of insufficient quantity to cardiovert the atria but of sufficient quantity so as to be discernable by the patient; and lead means for establishing electrical contact with the atria and wherein said warning electrical energy and said cardioverting electrical energy are both applied to said lead means.

14. A method of providing cardioverting electrical energy to at least one chamber of a patient's heart in need of cardioversion, said method including the steps of:

detecting activity of the at least one chamber of the patient's heart;

determining from the detected activity when the at least one chamber of the patient's heart is in need of cardioversion;

applying warning electrical energy to the at least one chamber of the patient's heart when the at least one chamber of the patient's heart is in need of cardioversion; and thereafter applying the cardioverting electrical energy to the at least one chamber of the patient's heart; wherein, the warning electrical energy is of insufficient quantity to cardiovert the at least one chamber but of sufficient quantity so as to be discernable by the patient.

15. A method as defined in claim 14 further including the step of delaying the application of said cardioverting energy until after at least a predetermined delay time elapses after applying the warning electrical energy.

16. A method of providing cardioverting electrical energy to at least one chamber of a patient's heart in need of cardioversion, said method including the steps of:

detecting activity of the at least one chamber of the patient's heart;

determining from the detected activity when the at least one chamber of the patient's heart is in need of cardioversion;

applying warning electrical energy to internal tissue of the patient when the at least one chamber of the patient's heart is in need of cardioversion; and thereafter applying the cardioverting electrical energy to the at least one chamber of the patient's heart; wherein, the warning electrical energy is of insufficient quantity to cardiovert the at least one chamber but of sufficient quantity so as to be discernable by the patient; and repeating said determining step after applying said warning electrical energy and applying said cardioverting electrical energy to the at least one chamber of the patient's heart if said repeated determining step determines that the at least one chamber is in need of cardioversion.

17. A method of providing cardioverting electrical energy to at least one chamber of a patient's heart in need of cardioversion, said method including the steps of:
   detecting activity of the at least one chamber of the patient's heart;
   determining from the detected activity when the at least one chamber of the patient's heart is in need of cardioversion;
   applying warning electrical energy to internal tissue of the patient when the at least one chamber of the patient's heart is in need of cardioversion; and thereafter
   applying the cardioverting electrical energy to the at least one chamber of the patient's heart; wherein,
   delaying the application of said cardioverting energy until after at least a predetermined delay time elapses after applying the warning electrical energy; wherein,
   the warning electrical energy is of insufficient quantity to cardiovert the at least one chamber but of sufficient quantity so as to be discernable by the patient, and wherein
   said predetermined delay time is between one minute and twenty minutes.

18. A method of providing cardioverting electrical energy to at least one chamber of a patient's heart in need of cardioversion, said method including the steps of:
   detecting activity of the at least one chamber of the patient's heart;
   determining from the detected activity when the at least one chamber of the patient's heart is in need of cardioversion;
   applying warning electrical energy to internal tissue of the patient when the at least one chamber of the patient's heart is in need of cardioversion; and thereafter
   applying the cardioverting electrical energy to the at least one chamber of the patient's heart;
   delaying the application of said cardioverting energy until after at least a predetermined delay time elapses after applying the warning electrical energy; wherein,
   the warning electrical energy is of insufficient quantity to cardiovert the at least one chamber but of sufficient quantity so as to be discernable by the patient; and
   repeating said determining step after said predetermined delay time elapses and applying said cardioverting electrical energy to the at least one chamber of the patient's heart if said repeated determining step determines that the at least one chamber is in need of cardioversion.

19. A method of providing cardioverting electrical energy to at least one chamber of a patient's heart in need of cardioversion, said method including the steps of:
   detecting activity of the at least one chamber of the patient's heart;
   determining from the detected activity when the at least one chamber of the patient's heart is in need of cardioversion;
   applying warning electrical energy to internal tissue of the patient when the at least one chamber of the patient's heart is in need of cardioversion; and thereafter
   applying the cardioverting electrical energy to the at least one chamber of the patient's heart; wherein,
   the warning electrical energy is of insufficient quantity to cardiovert the at least one chamber but of sufficient quantity so as to be discernable by the patient; and including the further steps of providing lead means, establishing electrical contact between said lead means and said at least one chamber of the patient's heart, and applying said warning electrical energy and said cardioverting electrical energy to said lead means.

20. A method of providing cardioverting electrical energy to at least one chamber of a patient's heart in need of cardioversion, said method including the steps of:
   detecting activity of the at least one chamber of the patient's heart;
   determining from the detected activity when the at least one chamber of the patient's heart is in need of cardioversion;
   applying warning electrical energy to internal tissue of the patient when the at least one chamber of the patient's heart is in need of cardioversion; and thereafter
   applying the cardioverting electrical energy to the at least one chamber of the patient's heart; wherein,
   the warning electrical energy is of insufficient quantity to cardiovert the at least one chamber but of sufficient quantity so as to be discernable by the patient; and including the further step of performing a protocol to establish that the patient's heart is in a nonvulnerable condition and wherein said protocol is performed prior to applying said warning electrical energy and is repeated prior to applying said cardioverting electrical energy.

21. A method for providing cardioverting electrical energy to the atria of a patient's heart in need of cardioversion, said method including the steps of:
   detecting atrial activity of the patient's heart;
   determining from the detected atrial activity when the atria of the patient's heart are in need of cardioversion;
   applying warning electrical energy to the atria of the patient's heart when the atria are in need of cardioversion; and thereafter
   applying cardioverting electrical energy to the atria of the patient's heart to cardiovert the atria; wherein
   said warning electrical energy is of insufficient quantity to cardiovert the atria but of sufficient quantity so as to be discernable by the patient.

22. A method as defined in claim 21 further including repeating said determining step after applying said warning electrical energy and applying said cardioverting electrical energy to the atria of the patient's heart if said repeated determining step determines that the atria are in need of cardioversion.

23. A method as defined in claim 22 further including the step of delaying the application of said cardioverting energy until after at least a predetermined delay time elapses after applying the warning electrical energy.

24. A method as defined in claim 23 wherein said predetermined delay time is between one minute and twenty minutes.

25. A method as defined in claim 23 further including repeating said determining step after said predetermined delay time elapses and applying said cardioverting electrical energy to the atria of the patient's heart if said repeated determining step determines that the atria in need of cardioversion.

26. A method as defined in claim 21 including the further step of providing lead means, establishing electrical contact between said lead means and the atria of the patient's heart, and applying said warning electrical energy and said cardioverting electrical energy to said lead means.

27. A method as defined in claim 21 including the further step of performing a protocol to establish that the patient's heart is in a nonvulnerable condition and wherein said protocol is performed prior to applying said warning electrical energy and is repeated prior to applying said cardioverting electrical energy.

28. A method as defined in claim 21 wherein said warning electrical energy has a quantity on the order of 0.1 joule and said cardioverting electrical energy has a quantity between 0.5 and one joule.

* * * * *